United States Patent [19]

Tökes et al.

[11] Patent Number: 4,460,560
[45] Date of Patent: Jul. 17, 1984

[54] DRUG DELIVERY BY POLYMERIC CARRIERS

[75] Inventors: Zoltán A. Tökes, Los Angeles; Kathryn E. Rogers; Alan Rembaum, both of Pasadena, all of Calif.

[73] Assignee: University of Southern California, Los Angeles, Calif.

[21] Appl. No.: 389,537

[22] Filed: Jun. 18, 1982

[51] Int. Cl.³ .................. A61K 49/00; A61K 43/00
[52] U.S. Cl. .................................. 424/1.1; 424/9; 424/16; 424/31; 424/32; 424/78; 424/80; 424/81; 424/82; 424/83
[58] Field of Search .................. 424/1.1, 9, 16, 31, 424/32, 78, 80, 83

[56] References Cited

U.S. PATENT DOCUMENTS

| | | | |
|---|---|---|---|
| 3,105,801 | 10/1963 | Bell | 204/154 |
| 3,853,987 | 12/1974 | Dreyer | 424/1 |
| 3,957,741 | 5/1976 | Rembaum | 526/312 |
| 4,046,722 | 6/1977 | Rowland | 424/55 |
| 4,108,972 | 8/1978 | Dreyer | 424/1 |
| 4,267,235 | 5/1981 | Rembaum | 428/407 |
| 4,291,024 | 9/1981 | Turcotte | 424/180 |
| 4,310,505 | 1/1982 | Baldeschwieler et al. | 424/1 |
| 4,310,506 | 1/1982 | Baldeschwieler et al. | 424/1 |
| 4,331,648 | 5/1982 | Myers, Jr. et al. | 424/180 |
| 4,343,895 | 8/1982 | Sugaar | 435/6 |
| 4,377,567 | 3/1983 | Geho | 424/1 |

FOREIGN PATENT DOCUMENTS

| | | | |
|---|---|---|---|
| 0046506 | 11/1981 | European Pat. Off. | 424/180 |
| 1541435 | 2/1979 | United Kingdom | 424/55 |

OTHER PUBLICATIONS

Allen et al., Biochim. Biophys. Acta, 643, (1981), 346-362.
Pitha et al., Journal of the National Cancer Institute, 65, (1980), 1011-1015.
Hartmann et al., Chem. Abstracts, 97, (1982), #56345m.
Molz, et al., Chem. Abstracts, 94, (1981), #4270b.
DiMarco, Biochem. Pharmacol., 20, (1971), 1323-1328.
Bachur et al., Proc. Natl. Acad. Sci. U.S.A., 76, (1979), 954-957.
Murphree et al., Biochem. Pharmacol., 25, (1976), 1227-1231.
Kessel, Mol. Pharmacol., 16, (1979), 306-312.
Tritton et al., Biochem. Biophys. Res. Comm., 84, (1978), 802-808.
Senyei et al., J. Pharmaceutical Sci., 70, (1981), 389-391.
Widder et al., Proc. Natl. Acad. Sci. U.S.A., 78, (1981), 579-581.
S. Margel, et al., "Polyglutaraldehyde: A New Reagent for Coupling Proteins to Microspheres and for Labeling Cell-Surface Receptors. II. Simplified Labeling Method by Means of Non-Magnetic and Magnetic Polyglutaraldehyde Microspheres"; Journal of Immunological Methods, 28, pp. 341-353, 1979.
A. DiMarco, "Adriamycin (NSC-123127): Mode and Mechanism of Action", Cancer Chemotherapy Reports, Part 3, vol. 6, No. 2, Oct. 1975.

Primary Examiner—Christine M. Nucker
Attorney, Agent, or Firm—Nilsson, Robbins, Dalgarn, Berliner, Carson & Wurst

[57] ABSTRACT

Anthracycline cancer drugs are covalently coupled to polymeric particles having a diameter of greater than about 0.5 microns to produce pharmaceutical preparations having enhanced cytostatic activity. The coupling of drugs to polymeric carriers shows increased activity against cancer cells, allows the bound drug to retain its cytostatic activity after repeated uses and shows an increase in activity against drug resistant cells.

18 Claims, 3 Drawing Figures

DRUG DELIVERY BY POLYMERIC CARRIERS

FIELD OF THE INVENTION

This invention relates generally to agents useful in chemotherapy as well as in clinical analysis, and more particularly to the preparation, in vivo administration, and in vitro utilization of drugs immobilized on polymers.

BACKGROUND AND SUMMARY OF THE INVENTION

Chemotherapeutic agents have long been known to operate through intracellular chemical processes such as enzyme inhibition or other protein binding which require the transport of the preparation through the cell wall to reach the cytoplasm or nucleus of the organism. Cytostatic and cytotoxic preparations such as anti-tumor drugs are thought to inhibit neoplastic growth by the intracellular DNA breakage which results in the inhibition of DNA replication and/or RNA synthesis. A. DiMarco, Cancer Chem. Rep. 59, 91–106 (1975); and A. DiMarco et al, Biochem. Pharmacol. 20, 1323–1328 (1971). For example, it has been proposed that the antibiotic drug doxorubicin, an aminoglycosidic anthracycline, affects tumor growth through DNA or RNA binding or through lipid peroxidation. R. A. Bachur et al, Proc. Natl. Acad. Sci. USA. 76, 954–957 (1979). It has also been shown that doxorubicin may have some of its effect through interaction on the cell surface membrane. S. A. Murphree et al, Biochem. Pharmacol. 25, 1227–1231 (1976); D. Kessel, Mol. Pharmacol. 16, 306–312 (1979); and J.R. Tritton, Biochem. Biophys. Res. Comm. 84, 802–808 (1978).

It has now been found that pharmaceutical preparations may be covalently bonded to form stable drug polymer complexes which appear to operate by a different mechanism than given above and which demonstrate an advantageous increase in cytostatic and cytotoxic effectiveness as compared to the free drug by increasing perturbance of the membranous domains of a target cell or microorganism. The drug polymer complexes of the present invention may be formed by the coupling of the drugs to various polymeric backbones, dependent upon the functional chemical groups and reactivity of the individual pharmaceutical preparation. The coupling of the drug to the backbone substantially eliminates the presence of the free drug in the preparation, and the polymers are of sufficient size that the molecules are incapable of being transmitted through membrane barriers, such as the cell, nuclear, mitochondrial, lysosomal, and endoplasmic membranes, to have an intracellular effect. Thus, it is believed that the coupled drug sufficiently perturbs the cell membrane to have novel cytostatic and cytotoxic effects.

Of course, it has been known (e.g. Dreyer U.S. Pat. Nos. 3,853,987 and 4,108,972) to bind polymeric microspheres with such agents as antigens and antibodies to serve as reagents in immunoassay determinations. However, it is believed to be unique to utilize polymeric substances to limit access of a drug to the membranous regions of a cell either for treatment or for analytical purposes.

With regard to therapeutic effects, the interaction between the high density of drug particles on the polymer surface and the cell results in multiple and repetitious binding at the cell surface which leads to increased cytotoxic activity. Among other advantages, a ten- to one thousand-fold increase in cytostatic activity was shown with various human and animal cancer cells. The drug is not modified or uncoupled from the polymer during cellular interaction, allowing extended use of the preparation and a substantial increase of the half-life of the drug in circulation. In addition, the polymer-bound drug may provide a differential toxicity towards tumor cells and has been shown to overcome various forms of drug resistance. For example, major forms of drug resistance include: (1) decreased transport at the cell surface for inhibition at the port of entry, (2) increased intracellular metabolic degradation of the drug, (3) increased synthesis of target molecules (diluting out the toxic effect of the drug), and (4) increased efflux of the drug.

The polymeric carriers of the present invention may be any molecule which is of sufficient size and which is capable of coupling drugs in a manner which will provide the described drug-cell or microorganism interaction. Specifically, examples include polyglutaraldehyde, polyhydroxyethylmethacrylate, polyacrolein, polymers of glucuronic acid, polymers of hexose and/or hexose amines, polyamino acid, and starch or vinyl pyrolidone polymeric beads containing aldehyde functional groups such as hydroxyl, carboxyl, amine, sulfhydril, azide or aldehyde, which serve to covalently bind the desired drug. The monomers of the compounds are capable of polymerizing while retaining or forming functional groups. In this regard, polyglutaraldehyde has proven particularly useful in that the glutaraldehyde monomer undergoes a spontaneous reaction upon polymerization to form functional aldehyde groups.

Any drug may be selected which will bond to the polymer as hereinafter described, and which will cause the resulting drug-polymer complex to attach to and disrupt the cell membrane so as to afford the novel effects demonstrated herein.

The drug polymers of the present invention are useful in applications where cellular destruction or the inhibition of cellular growth is desired. For example, the drug polymers may be used to kill or inhibit the growth of bacteria or other such microorganisms either in vitro or in vivo. Similarly, infected animal cells may be affected or treated and the growth of tumor cells may be effectively inhibited. While we do not desire to be restricted to a particular theory of cellular effect, it can be hypothesized that the polymer presents the drug to the cell membranes as a mosaic and provides multiple and repetitious sites for drug-cell interactions which disrupt the critical functions of the cell and inhibit further growth and division of the cell.

As above indicated, the invention has other, non-therapeutic utility, for example in the assessment of drug sensitivity. In particular, sensitivity to a drug can be assayed by a procedure in which the affinity of the drug to the cell surface is quantitated by measuring the amount of drug actually retained on the cell membranes. These measurements can be conveniently performed with the polymer drug complexes. Tracers, such as isotopes, fluorescent markers, or heavy metals, can be incorporated into the polymers. These tracers will allow direct correlation with the drug-binding properties of the cell membranes which properties reflect on the cell sensitivity to a given drug.

These and other features and advantages of the invention will become apparent from the following detailed description. In the present specification, the term "cell"

is used in its broadest sense and is meant to include both eucaryotic and procaryotic cells.

DETAILED DESCRIPTION

Figure 1:
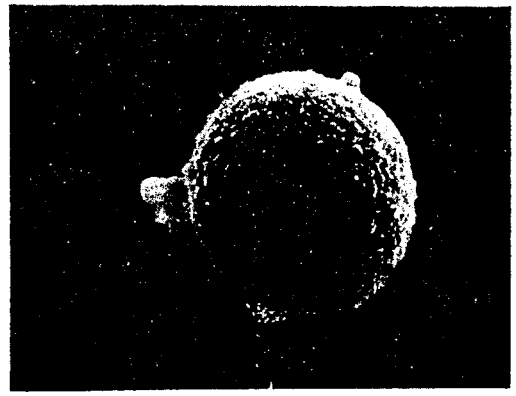
FIG. 1 is a scanning electron micrograph of an untreated hepatocyte.

The organic polymeric carriers of the present invention may be made by several methods. Generally, the carriers must be of an appropriate size to enable the cell wall interaction of the coupled drug and preferably having a diameter in the range of about 100 Angstroms to 1.5 microns. The carriers must be stable and not aggregate in reaction or culture media, or in the presence of physiological fluids. Another requirement is that the carriers be biocompatible i.e. there not be undesired reactions with body fluids or cells, e.g. the polymers should not be degradable to toxic products. In addition, the carrier must include a functional group or groups capable of bonding with the coupling groups on the drug without disabling the therapeutic effectiveness thereof; in fact, the pharmacological properties are improved. In this regard, spherical microscopic particles have proven to be eminently useful, but the usefulness of polymers in this invention is not limited to a spherical shape.

Such polymers may be made by emulsion polymerization, ionizing radiation, or by aldol condensation reactions. The ionizing radiation method has certain advantages in that the microspheres produced are relatively free of impurities, as the reaction does not require an emulsifier or free radical initiator. However, each technique yields polymers having one or more functional groups, such as, but not limited to, those functional groups listed above, on the surface which can be utilized to covalently bind drugs according to the Schiff's-base reaction or by other methods hereinafter described.

The emulsion polymerization of hydroxyethylmethacrylate (HEMA) is fully described in U.S. Pat. No. 3,957,741, the specification of which is hereby incorporated by reference. Generally, the polymerization is carried out in an aqueous medium containing HEMA, methylmethacrylate and methacrylic acid. Ethylene glycol dymethacrylate in small amounts is added as a cross-linking agent. A free radical polymerization initiator (e.g. ammonium persulphate) and an emulsifier are also used. The size of the particles is directly dependent on the concentration of the monomers used in the reaction. Also described in the above-mentioned patent is the production of microspheres through the cobalt 60 irradiation of HEMA dissolved in water. In that regard, polymerization proceeds by the application of from 0.05 to 1.0 megarads of radiation from a cobalt gamma source under oxygen-excluding conditions. HEMA polymers contain hydroxyl, carboxyl and amine functional groups. Polyglutaraldehyde microspheres may be prepared by similar techniques, as hereinafter described, and contain an aldehyde functional group. In selecting the proper drug-polymer combination, the polymer chosen should be capable of binding the drug while allowing the effective portion of the drug molecule to remain functional.

Also useful in the present invention are polymeric particles known as polyvinyl pyrolidone and polyacrolein microspheres.

A process for polymerizing unsaturated aldehydes such as acrolein is disclosed in U.S. Pat. No. 3,105,801 to Bell et al, the specification of which is hereby incorporated by reference. The process comprises adding a small amount of acid or an acid-acting material to an aqueous solution containing acrolein or other unsaturated aldehyde and exposing the acidic medium to high energy ionizing radiation to form high molecular weight polymer in the form of light powders having non-uniform shapes and sizes. Bell et al also discusses the copolymerization of acrolein with a wide variety of ethylenically unsaturated monomers such as ethylene diamine, pyridine or acrylic acids or esters, vinyl halides, etc. in amounts from 0.1 to 60%, preferably from 1% to 25% by weight of the monomer mixture.

Initiation of acrolein copolymerization by high energy radiation (i.e. cobalt 60 gamma source in doses of from 0.05 to 2.0 megarads) in the absence of chemical initiators or acid materials provides a pure and evenly shaped microsphere. The microspheres may be produced by addition polymerization of a liquid polymerization system and may include a dispersion of the metal particles in a monomer mixture containing a covalently bondable unsaturated monomer. More uniformly sized and shaped beads are formed in very dilute aqueous monomer mixtures of no more than 5% by weight, preferably 1 to 4% by weight of dissolved monomers.

While the invention will be exemplified by reference to specific examples of the production of polyglutaraldehyde microspheres covalently bound to doxorubicin, the invention in general and certain aspects in particular are broad in scope, for example, the concept of the binding of chemotherapeutic agents to linear, amorphous, branching or microspheric polymeric backbones to produce formulations having the effects hereinafter set forth. Consequently, specific details afford the best embodiments known at this time to provide a basis for the claims which define the scope of the present invention.

Synthesis of Polyglutaraldehyde Polymers

The synthesis of polyglutaraldehyde microspheres is described in the *Journal of Immunological Methods*, 28 (1979) 341–353 and U.S. Pat. No. 4,267,235, both of which are hereby incorporated by reference.

EXAMPLE 1

100 ml of 5% aqueous glutaraldehyde solution, containing 1% Aerosol 604, was treated with sodium hydroxide until a pH of eleven was attained. The mixture was then deaerated with nitrogen, and placed on a mechanical shaker for 24 hours at room temperature in a tightly closed container. During this time the pH was periodically readjusted to eleven by the addition of sodium hydroxide. The mixture was subsequently washed extensively with 100 volumes of double-distilled water. The washed microspheres were then sonicated at 30° C. for two minutes using a needle-probe sonicator (Braun Sonic-1410) set at 100 watts. After sonication, the microspheres were passed through a 1.2 Millipore filter disc using vacuum filtration apparatus. The filtrate was collected and resuspended in 20% bovine serum albumin. This mixture was then centrifuged at 88×g for ten minutes and the supernate contains smaller polymers which can be further processed for dry coupling. The pellet was resuspended in double-distilled water and repeatedly washed in 200 volumes of water. The synthesis yielded a population of microspheres ranging in diameter from approximately 0.1 to 1.0 microns, with greater than 90% of the microspheres having a diameter of between 0.25 and 0.65 microns. The mean diameter was estimated to be 0.45 microns as determined by small angle light scattering using laser flow cytometry. This mean diameter was subsequently confirmed by scanning electron microscopy.

EXAMPLE 2

In a manner similar to the procedure described in EXAMPLE 1, water soluble linear gluteraldehyde polymers were prepared by raising the concentration of the aqueous glutaraldehyde solution to 20%, and treating with sodium hydroxide until a pH of 13 was obtained. Such polymers are useful, when coupled to drugs as hereinafter described, in applications where increased water solubility of the complex is desired.

Drug-Polymer Coupling

EXAMPLE 3

A solution of doxorubicin was prepared by dissolving 6 mg of doxorubicin hydrochloride in 5 ml double-distilled water and adjusting the pH to 6.5 with 0.1 N hydrochloric acid. 100 mg of the polyglutaraldehyde microspheres were added to the solution and reacted for 2½ hours with continuous shaking. This reaction was terminated by centrifugation at 9500×g for 30 minutes.

The concentration of the free doxorubicin in solution was determined by spectrofluorescence, and the initial binding efficiency was determined to be 60 nmol of doxorubicin per 1 mg of the microspheres. Noncovalently bound doxorubicin was removed by subsequent detergent and liposome washes. The microspheres were first treated with 10 mls of 0.5% NP-40 detergent for two hours. Liposomes containing phosphatidylserine, phosphatidylcholine and cholesterol in a 2-6-3 molar ratio were reacted with microspheres for one hour at room temperature. Liposomes containing absorbed free doxorubicin were dissolved in acetone and extracted with chloroform. The extract was concentrated and rediluted in ethanol. The doxorubicin covalently bound to the microspheres was quantitated by difference after determining the concentration of the doxorubicin in the reaction solution and in each wash.

After these purification steps, the coupling efficiency of the covalently bound doxorubicin was 43 nmol doxorubicin per 1 milligram microspheres. This represents approximately 9.7 times $10^6$ molecules of doxorubicin bound to a microsphere with an average diameter of 0.45 microns. Since it is assumed that the polyglutaraldehyde microspheres are essentially perfect spheres and that the doxorubicin would bond at the surface thereof, this results in an approximate density of two molecules of bound doxorubicin per 0.01 micron$^2$ of polyglutaraldehyde.

The nature of the bond between the microspheres and the covalently bound doxorubicin was then examined. To verify the functional aldehyde group of the microsphere as the binding site, LiBH$_4$ was used for the reduction of aldehyde groups to corresponding alcohol groups. Although doxorubicin could apparently still be bound to the reduced microspheres, the initial binding efficiency was less than 10 nmol per 1 mg of the microspheres. Subsequent detergent and liposome washes completely removed the doxorubicin from the microspheres. This observation indicates that the aldehyde groups of the polyglutaraldehyde microspheres are required for the covalent binding.

Doxorubicin has two possible functional sites whereby the drug may be bound to the polyglutaraldehyde microspheres. The first is the hydroxyl group attached to the acetyl group found at the eighth position of the anthracycline ring, and the second is the amino group found at the third position of the sugar moiety. In order to determine the functionality of these groups, identical coupling experiments were made using the doxorubicin analogs daunorubicin and N-acetyl daunorubicin. Daunorubicin is identical to doxorubicin with the exception that the hydroxy of the hydroxyacetyl group at the eighth position on the anthracycline ring is not present. N-acetyl daunorubicin is identical to doxorubicin except that the reactive amino group on the daunosamine sugar is acetylated. Since both doxorubicin and daunorubicin were found to similarly couple to the microspheres, it was assumed that the hydroxyl group was not involved in the binding. However, when N-acetyl daunorubicin was reacted with polyglutaraldehyde microspheres in the above-described manner, the amount of covalently linked drug produced was below detectable levels. From this data it was concluded that the covalent coupling of doxorubicin to the polyglutaraldehyde microspheres occurs between the amino group on the drug and the aldehyde on the polymer. Therefore, the most likely coupling mechanism is a Schiff's-base condensation which forms a stable imino complex.

Stability of the Covalent Bond

After determining that the drug was covalently bound to the microspheres, the stability of the bond was tested under cell culture conditions. Specifically, experiments were conducted to determine whether cells incubated with doxorubicin polyglutaraldehyde polymers are capable of removing the drug from the microspheres.

EXAMPLE 4

The stability of the bound drug of EXAMPLE 3 in contact with cells was tested by incubation in suspension cultures for 24, 48 and 72 hours. The cell lines used were CCRF-CEM, CCRF-CEM/Vbl 500, CCRF-CEM/Vbl 100, sarcoma-180 and L1210 cells. Following incubation, the cells and the microspheres were co-sedimented at 3600×g for 30 minutes, lysed with 50 ml of 0.5% NP-40, and disrupted by sonication. Doxorubicin released by the cells was then extracted into a 70% ethanol/0.45N hydrochloric acid solution and quantified by spectrofluorescence. Control experiments utilized a similar procedure using cells with plain microspheres and cells with free doxorubicin and plain microspheres. The control studies demonstrated that 100% of uncoupled doxorubicin can be recovered from the assays.

Specifically, microspheres containing $10^{-6}$M doxorubicin were incubated with $6\times10^4$ cells in 2 ml of RPMI-1640 cell culture medium supplemented with 2% fetal calf serum and 8% newborn calf serum. After various times, the cells were removed from the culture, lysed with 0.5% NP-40 detergent, and disrupted by sonication. The free doxorubicin was extracted with an ethanol/hydrochloric acid solution from the cell lysate and the culture supernate. The concentrations of released doxorubicin are expressed in Table 1 as a percentage of the total bound drug.

TABLE 1

Amount of Doxorubicin Released from Microspheres by Various Cell Lines

|  | 0.1 Hr. | 24 Hr. | 48 Hr. | 72 Hr. |
|---|---|---|---|---|
| L1210 | 0.03% | 0.03% | 0.03% | 0.03% |
| S-180 | 0.08 | 0.06 | 0.03 | 0.07 |
| CCRF/CEM | 0.03 | 0.01 | 0.03 | 0.08 |
| CCRF-CEM/Vbl 500 | 0.02 | 0.03 | 0.03 | 0.02 |
| CCRF-CEM/Vbl 100 | 0.03 | 0.03 | 0.03 | 0.03 |

Further tests showed that after 96 hours, less than 0.1% (1.0 nmol) of the drug had been released from the microspheres into the cell lysate. Incubations of the coupled drug in RPMI-1640 medium, phosphate buffered saline or fetal calf serum in the absence of cells failed to release detectable amounts of doxorubicin (less than 20 picomoles). Coupled microspheres not treated with liposomes prior to cell culture released a significantly higher amount of free doxorubicin. Therefore, the drug-polymer complexes prepared by the described method display increased stability during cell culture conditions.

Cytotoxic Activity

Cytotoxic effects of the microspheres of EXAMPLE 3 and free doxorubicin were investigated using short-term monolayer cultures established from the livers of normal rats and rats which had been fed 2-AAF or DEN. Cell viability was evaluated by trypan blue exclusion and confirmed by $^{51}Cr$ release. TABLE 2 illustrates the high correlation between viability determined by the two techniques.

EXAMPLE 5

Male Fischer 344 rats weighing 150 to 200 g were used to obtain viable hepatocytes. The animals were fed a basal, high-casein diet. A 12-hr light cycle was maintained in the animal colony and water was given ad libitum. Carcinogen altered hepatocytes were produced by feeding the animals a diet containing 0.02% 2-AAF (w/w) or 80 ppm DEN in the drinking water for 8 to 12 weeks. Cells from such animals were used in the cytotoxicity and cell viability studies reported herein.

Liver cell suspensions were prepared by the collagenase perfusion technique. Cell suspensions were passed through sterile gauze filters to remove large tissue pieces. Viability was assessed by trypan blue exclusion and perfusates containing less than 65% viable cells were not used. Cells were plated at density of $1 \times 10^6$ viable cells per plastic culture flask of 25 cm$^2$ surface area in 4 ml of L-15 medium containing 3.5 mg/ml 4-(2-hydroxyethyl)-1-piperazineethanesulfonic acid and 2 mg/ml bovine serum albumin. The medium was supplemented with 10% fetal bovine serum, 100 μg/ml penicillin, and streptomycin. Following a 2 hour attachment period at 37° in a water-saturated 5% $CO_2$-95% air incubator, the cells were washed twice with medium and placed in 4ml of fresh medium supplemented with 200 μl PBS, free doxorubicin, uncoupled microspheres, or the polymer bound drug. At various times 0.8 ml of trypan blue was added to each flask and incubated for 10 minutes at 37°. The medium was removed and the number of viable cells was counted.

$^{51}Cr$ in the form of sodium chromate in sterile isotonic saline was added to the cell suspensions at a concentration of 100 μCi/0.5 ml/$5 \times 10^6$ cells. The cells were then incubated at 37° for 1 hour with constant shaking. After labeling, the supernatent was removed by centrifugation at $350 \times g$ for 5 min and the cells were washed a minimum of 5 times in L-15 medium. Labeled cells were then aliquoted into culture flasks and allowed to attach as previously described. At various times 250 μl aliquots were removed from the flasks and counted in a Packard Gamma Counter. As a control for complete $^{51}Cr$ release, 0% cell viability, cells were detached from the culture flask surface with 10% trypsin and subsequently lysed with 0.5% Nonidet P-40 followed by sonication. Total $^{51}Cr$ release was obtained by subtraction of the residual radioactivity which remained associated with the cell debris.

TABLE 2

Comparison of cell viability measured by Trypan blue exclusion and $^{51}Cr$ release
Results are the average values from two experiments

| | | Percent viability measured by | |
|---|---|---|---|
| Drug Treatment | Incubation time (hr) | Intracellular $CR^{51}$ | Dye Exclusion |
| Free doxorubicin | 3 | 100 | 100 |
| | 5 | 96 | 99 |
| | 8 | 86 | 81 |
| | 12 | 75 | 72 |
| | 18 | 57 | 59 |
| Covalently bound doxorubicin microspheres | 3 | 97 | 93 |
| | 5 | 89 | 80 |
| | 8 | 82 | 73 |
| | 12 | 70 | 65 |
| | 18 | 64 | 64 |

EXAMPLE 6

Hepatocytes in perfusates obtained from rats which had been fed the dietary carcinogen 2-AAF are highly resistant to the cytocidal effects of doxorubicin. Experiments were performed to determine the toxicity of the doxorubicin microspheres with regard to these resistant hepatocytes. Data from TABLE 3 indicates that the cells are more sensitive to polymer-bound Adr than to the free drug. Concentrations of free doxorubicin must be approximately 100-fold higher than the polymer-bound drug to decrease viability to 50%. The most significant differences in cytotoxicity occurred at a concentration of $10^{-5}M$ where the free drug treated hepatocytes remained unaffected and polymer-bound doxorubicin decreased viability to 47%. Subsequent experiments were done with $10^{-6}M$, free or bound drug, to approach clinically relevant concentrations.

TABLE 3

Comparison of concentration effects of the bound to free drug using carcinogen altered drug-resistant hepatocytes. The percentage survival of attached cells was compared to controls after a 24-hr exposure to the drug.

| | % Viability | |
|---|---|---|
| Concentration (M) | Free Drug | Bound Drug |
| $10^{-7}$ | 100 | 85 |
| $10^{-6}$ | 100 | 74 |
| $10^{-5}$ | 100 | 47 |
| $10^{-4}$ | 68 | 32 |

EXAMPLE 7

Cell kill kinetics of normal rat hepatocytes with both free and polymer-bound drug are shown in TABLE 4. These studies are not continued for longer than 24 hours due to the rapid natural decline in viability observed with untreated cells after prolonged cell culture. The viability of untreated control cultures remained constant throughout each experiment. Addition of the bound drug to the cultures resulted in an immediate increase in cell death. However, cell viability in the presence of free drug was not affected during the first 4 hours of treatment. Alternatively, at 24 hours only 10% of the cells treated with free drug remained viable while 64% of those treated with the bound drug were unaffected. Cell viability was not influenced by addition of uncoupled microspheres to the cultures.

TABLE 4

Time-survival response of normal hepatocytes exposed to the bound or free drug. The percentage survival of attached cells was compared to controls after various times of exposure to the drug. Each point is the mean of at least 3 determinations.

| Time (hours) | % Viability Free Drug | % Viability Bound Drug |
|---|---|---|
| 2 | 99 | 93 |
| 4 | 98 | 84 |
| 6 | 91 | 80 |
| 8 | 81 | 73 |
| 12 | 72 | 65 |
| 18 | 59 | — |
| 24 | 10 | 46 |

EXAMPLE 8

Cell kill kinetics of hepatocytes made resistant by 2-AAF feeding are depicted in TABLE 5. At a concentration of $10^{-6}$M the free drug had no detectable killing effect on these cells up to 24 hours. However, addition of the bound drug resulted in a rapid declined in cell viability. At 24 hours, only 67% of the cells remained viable. When hepatocytes made resistant by DEN feeding were used, the same results for free and polymer-bound Adr at $10^{-6}$M were obtained. Free doxorubicin had no killing effect on these cells at 24 hours, while the bound drug decreased viability to 55%±1.7 s.d.

TABLE 5

Time-survival response of resistant hepatocytes exposed to the bound or free drug. The percentage survival of attached cells was compared to controls after various times of exposure to the drug. Each point is the mean of 3 determinations.

| Time (hours) | % Viability Free Drug | % Viability Bound Drug |
|---|---|---|
| 2 | 100 | 88 |
| 3 | 100 | 87 |
| 4 | 100 | 85 |
| 6 | 100 | 82 |
| 8 | 100 | 78 |
| 16 | 100 | 77 |
| 22 | 100 | 68 |
| 24 | 100 | 67 |

Cytostatic Activity

It is of significance that the drug-polymer complex retained the full activity of the free drug, as judged by cytostatic assays using three sensitive cell lines and two cell lines which were resistant to the action of the free drug. In the case of the sensitive CCRF-CEM, L1210 and S-180 cell lines, the covalently coupled doxorubicin was equally efficient as the free drug in the cytostatic assay. For the resistant CCRF-CEM/Vbl 500 and CCRF/CEM/Vbl 100 cell lines, the doxorubicin-microspheres were approximately ten times more active than free doxorubicin.

EXAMPLE 9

In order to test the cytostatic activity of the microspheres, $IC_{50}$ determinations were made with both the free drug and the drug-polymer complexes. All cell lines were maintained in suspension cultures in RPMI-1640 medium supplemented with the 2% fetal calf serum, 8% newborn calf serum, 0.5 mg/ml penicillin-streptomycin, and 0.015 mg/ml fungizone. The cells were diluted to 40,000 cells/assay/1.8 ml medium and an amount of free doxorubicin, doxorubicin-microspheres or plain microspheres was added in 0.2 ml of phosphate buffered saline. After 4 to 6 doubling times had elapsed, the remaining cells were counted on a Coulter counter. A ratio of the number of cells after incubation per the number of cells originally introduced (Nt/No) was obtained. The drug concentration required for 50% inhibition of cell growth ($IC_{50}$) was calculated according to the formula $$IC_{50} = \frac{Nc/No - 1}{2} + 1.$$

Table 6 shows the $IC_{50}$ values for free and coupled doxorubicin, wherein the $IC_{50}$ values represent the average of three determinations.

TABLE 6

| Cell Lines | $IC_{50}$ Free Drug | $IC_{50}$ Coupled Drug |
|---|---|---|
| L1210 | $2.8 \times 10^{-8}$M | $1.5 \times 10^{-8}$M |
| S-180 | $2.3 \times 10^{-8}$M | $5.6 \times 10^{-8}$M |
| CCRF-CEM | $1.1 \times 10^{-8}$M | $1.2 \times 10^{-8}$M |
| CCRF-CEM/Vbl 500 | $3.2 \times 10^{-7}$M | $2.0 \times 10^{-8}$M |
| CCRF-CEM/Vbl 100 | $3.9 \times 10^{-7}$M | $2.0 \times 10^{-8}$M |

When the coupled doxorubicin microspheres were recovered from the $Ic_{50}$ determination hereinbefore described and recycled for a second cytostatic assay, they continued to retain their full activity. These findings show that intracellular insertion or DNA intercalation of anti-tumor drugs are not essential for their pharmacological action, and the fact that the drug polymers of the present invention may be recycled and reused in the cytostatic assays which demonstrates that the drug remains bound to the polymer during all phases of cell growth and death. The polymer-coupled drug of the described embodiment is inaccessible to the nuclear material of the cell since the drug-polymer complex of EXAMPLE 3 has a minimum size of from approximately 0.1 to 1.5 microns and the cell membranes cannot generally transport structures larger than roughly 0.05 microns.

Growth Inhibition Studies

EXAMPLE 10

Cell lines used were the human leukemia clones CCRF-CEM/Vbl 500 and CCRF-CEM/Vbl 100 and rat liver cancer cells (RLC). All cultures were maintained in RPMI-1640 medium supplemented with fetal calf serum (2%), newborn calf serum (8%), penicillin-streptomycin (0.5 mg/ml), and fungizone (0.015 mg/ml)

(Flow Laboratories Inc.). Suspension cultures were diluted to $4 \times 10^4$ cells/assay/1.8 ml medium and attached cell lines were plated at $2.5 \times 10^5$ cells/25 cm² growth area/3.6 ml medium. Appropriate quantities of free doxorubicin, microsphere coupled doxorubicin, plain polyglutaraldehyde microspheres, or PBS, were added and the assays were incubated for 3–6 doubling times at 37° in a 5% $CO_2$ - 95% air incubator. Cells were then counted on a Model $Z_b$ Coulter counter and a ratio of total number of cells after incubation per number of cells originally introduced ($N_t/No$) was obtained.

The cell lines CEM/Vbl 100 and CEM/Vbl 500 were used in cytostatic assays to determine differences in growth inhibition properties between free doxorubicin and polymer-bound drug. Both cell lines are resistant to the effects of vinca alkaloids and are cross-resistant to Adr. Results in TABLE 7 demonstrate that free and polymer-bound doxorubicin are equally effective growth inhibitors at the higher drug concentrations. At free drug concentrations of $10^{-7}M$, growth inhibition of CEM/Vbl 100 was less than 22% and for CEM/Vbl 500 was less than 32%. However, using $10^{-7}M$ of the coupled drug, the growth inhibition for both cell lines is greater than 50%. At $10^{-8}M$, polymer bound doxorubicin inhibits growth 4–10 times more effectively than free drug. In addition the polymer-bound drug demonstrated significant growth inhibition at $10^{-9}M$ where there was no effect with the free drug. Each experiment was performed three times and drug concentrations were tested in duplicate.

TABLE 7

| Cell line | Drug Concentration | % Inhibition of growth Free Drug | Polymer Bound Drug |
|---|---|---|---|
| CEM/ | $10^{-5}$ | 98 | 100 |
| Vbl 100 | $10^{-6}$ | 86 | 86 |
|  | $10^{-7}$ | 22 | 54 |
|  | $10^{-8}$ | 3 | 30 |
|  | $10^{-9}$ | 5 | 25 |
|  | $10^{-10}$ | 0 | 4 |
| CEM/ | $10^{-5}$ | 81 | — |
| Vbl 100 | $10^{-6}$ | 67 | 72 |
|  | $10^{-7}$ | 32 | 66 |
|  | $10^{-8}$ | 14 | 54 |
|  | $10^{-9}$ | 0 | 22 |
|  | $10^{-10}$ | 0 | 14 |
|  | $10^{-11}$ | 0 | 0 |

EXAMPLE 11

The cytostatic activity of the drug polymer complex of EXAMPLE 3 was further investigated using the rat liver cancer cell line RLC. These cells were found to be unusually resistant to free Adr, as shown in TABLE 8. The 50% inhibitory concentration ($IC_{50}$) for the free drug was $1.8 \times 10^{-5}M$. In contrast, the $IC_{50}$ for the polymer-bound drug was $1.8 \times 10^{-8}M$, which represents a one-thousand-fold increase in cytostatic activity. Furthermore, the Adr-PGLs retained growth inhibition properties at concentrations as low as $1 \times 10^{-9}M$.

TABLE 8

| Concentration [M] | % Inhibition of Growth Free Drug | Polymer-Bound Drug |
|---|---|---|
| $10^{-3}$ | 100 | — |
| $10^{-4}$ | 80 | 96 |
| $10^{-5}$ | 36 | 95 |
| $10^{-6}$ | 22 | 94 |
| $10^{-7}$ | 0 | 92 |
| $10^{-8}$ | 0 | 51 |

TABLE 8-continued

| Concentration [M] | % Inhibition of Growth Free Drug | Polymer-Bound Drug |
|---|---|---|
| $10^{-9}$ | 0 | 14 |
| $10^{-10}$ | 0 | 0 |

Scanning Electron Microscopy

EXAMPLE 12

Sterile circular coverslips, 18 mm in diameter were placed in the wells of a 12 well tissue culture cluster. Hepatocytes were plated onto the coverslips at a density of $5 \times 10^5$ viable cells/well and were allowed to attach for 3 hours at 37° in a water-saturated 5% $CO_2$-95% air incubator. The cells were incubated with free drug, plain microspheres or the polymer bound drug for 24 hours. Following incubation, the culture medium was replaced by 5% glutaraldehyde in 0.1M cacodylate buffer, pH 7.4. After 3 hours, the glutaraldehyde was removed and the cells were washed repeatedly in 0.1M cacodylate buffer. The cells and microspheres were made electron dense by incubation in 1% Osmium tetraoxide at 4° for 45 min. Samples were then dehydrated by gradually increasing ethanol concentration to 100% over 90 min. Subsequent to critical point drying the coverslips were mounted on aluminum stubs with silver conducting paint. Prior to viewing on a Semco scanning electron microscope, each sample was electroplated with gold-palladium alloy.

FIG. 1 is representative of cultured rat hepatocytes magnified 8,000 times. The cells are rounded and display a few scattered blebs. Characteristically, the microvilli are short and thick and completely cover the surface of the cell. Treatment of the hepatocytes with the polymer bound drug of EXAMPLE 3 produces the microscopic alterations shown in FIG. 2, which lead to cell death as shown in FIG. 3. The magnification in both FIGS. 2 and 3 is twice that of FIG. 1.

Figure 2:
FIG. 2 is a first scanning electron micrograph of an hepatocyte treated with the polymer-bound drug of the present invention.
Figure 3:
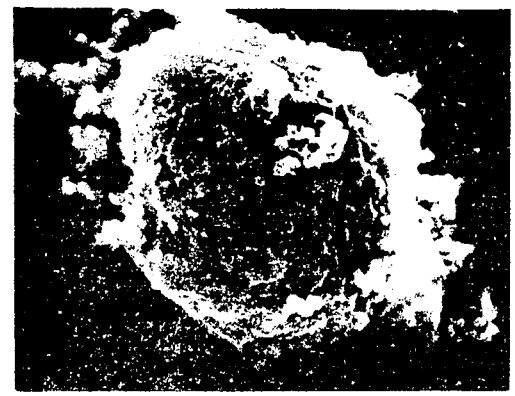
FIG. 3 is a second scanning electron micrograph of an hepatocyte treated with the polymer-bound drug of the present invention.

The majority of cells in the drug-polymer treated sample were blebbed and developed multiple holes and pits, similar to FIG. 2. Studies with the resistant hepatocytes demonstrated similar surface alterations. The majority of cells in the drug-polymer treated sample were blebbed. It is apparently this destruction of the cell surface that leads to cell death. Approximately 45% of the drug-polymer treated cells appeared to be non-viable. Treatment with polyglutaraldehyde microspheres alone did not cause blebbing.

As described herein, the polymer-bound preparations of the present invention increased the cytostatic activity of the drug ten-fold for both leukemia cell lines and one thousand-fold for the rat liver cancer cell line as measured by $IC_{50}$ determinations. The bound drug was able to inhibit greater than 90% of cell growth at concentrations where the free drug was completely ineffective. The polymer-bound drug remained active at concentrations lower than $10^{-9}M$ where the free drug had virtually no effect, even though the drug is bound in high density to a solid polymeric support and thus only a fraction of the drug concentration would be in direct contact with the cells. When carcinogen-altered drug-resistant rat hepatocytes were tested, the polymer-bound drug killed 53% of the cells at concentrations where the free drug had no effect, yet the bound drug was less toxic than the free drug to normal rat hepatocytes thus showing greater cytostatic activity with drug-resistant cells.

Utilization in Clinical Analysis

In accordance with another embodiment of the invention, as above indicated, the ability of the drug-carrying polymer to attach to cell membranes can be used as a significant indication of the sensitivity of a cell or microorganism to the toxic effects of the drug. The following example illustrates such a procedure.

EXAMPLE 13

Uncoupled PGL microspheres were radiolabeled using 1,3,46-Tetrachloro-e$\alpha$,6$\alpha$-diphenylglucouril (Iodogen). Test tubes were plated with 50 micrograms of Iodogen by rapidly evaporating the chloroform solvent. Approximately 25 mg of PGLs were added to each tube and the iodination reaction was initiated by the addition of 14 uCi of Na$^{125}$. The reaction was carried out at 21° C. for 10 min. with continuous agitation and stopped by transferring the microspheres to an Iodogen free tube. Excess radioactive Iodine was removed by repeated washing of the microspheres. Coupling efficiency of the labeling was found to be 12.5% by gamma emission counting. Following iodination, Adriamyicin was coupled to the microspheres.

Other tracer techniques can be used which include, for example, the incorporation of metal chelating side chains which allows the entrapment of heavy metals and the subsequent quantitation, by atomic absorption, of the polymers. Another example of a useful tracer technique is the incorporation of fluorescent tracers such as dansyl chloride, rhodamine, fluorescein isothiocyanate and other tracers disclosed in the above-referenced Dreyer U.S. Pat. Nos. 3,853,987 and 4,108,972, the disclosures of which are hereby incorporated by reference. The fluorescein polymers bond to the cell and become detectable and quantitatable using such equipment as a Fluorescent Activated Cell Sorter.

In addition to the drugs specifically mentioned above, the present invention has application to a wide variety of other drugs which are cytostatic and/or cytotoxic to a target cell or microorganism, including: methotrexate, vincristine, vinblastine, penicillin, glutamycin, and their cytostatic and/or cytotoxic analogs and homologs. Thus, one may follow the preparative procedure set forth in the above examples substituting any of these drugs for the doxorubicin of the examples.

Although the foregoing invention has been described in some detail by way of illustration and example, changes in form and the substitution of equivalents are contemplated as circumstances may suggest or render expedient; and although specific terms have been employed herein, they are intended in a descriptive sense and not for purposes of limitation, the scope of the invention being delineated in the following claims.

What is claimed is:

1. A pharmaceutical preparation in which the cytostatic or cytotoxic effect of a drug is improved by perturbing the membranous domains of a target cell or microorganism, comprising a drug covalently coupled to the surface of an organic polymer, in a manner such that the drug remains so coupled while having the cytostatic or cytotoxic effect on said toxic cell in the essential absence of endocytosis, the polymer being otherwise biocompatible with said cell and having a diameter in the range of about 100 angstroms to 1.5 microns, said preparation being essentially free of immunoglobulins.

2. The pharmaceutical preparation according to claim 1 wherein said organic polymer is selected from the group consisting of polyglutaraldehyde, polyhydroxyethylmethacrylate, polyacrolein, polymers of glucuronic acid, polymers of hexose or hexose amines, polyamino acid, and starch or vinyl pyrolidone polymeric beads containing functional groups effecting said covalent coupling.

3. The pharmaceutical preparation according to claim 1 wherein said drug is an anti-neoplastic chemotherapeutic agent.

4. The pharmaceutical preparation according to claim 2 wherein said organic polymer is in the form of microspheres.

5. The pharmaceutical preparation according to claim I wherein said organic polymer contains functional groups effecting said covalent coupling and selected from the group consisting of hydroxyl, carboxyl, amine, sulfhydril, azide or aldehyde alone or in combination.

6. The pharmaceutical preparation according to claim 1 wherein the drug is doxorubicin and the organic polymer is polyglutaraldehyde.

7. The method for the chemotherapeutic treatment of a subject which comprises administering to the subject an effective amount of pharmaceutical preparation of claim 1.

8. In a method for the administration of an antineoplastic drug to a subject having resistance to said drug, the improvement which comprises administering the drug in the form of a pharmaceutical preparation according to claim 1.

9. The method according to claim 7 or 8 wherein the organic polymer is selected from the group consisting of polyglutaraldehyde, polyhydroxyethylmethacrylate, polyacrolein, polymers of a glucuronic acid, polymers of hexose or hexose amines, polyamino acid, or starch or vinyl pyrolidone polymeric beads containing functional groups effecting said covalent coupling.

10. The method according to claim 9 wherein the polymer is in the form of microspheres.

11. The method according to claim 7 or 8 wherein the polymer contains functional groups selected from hydroxyl, carboxyl, amine, sulfhydril, azide or aldehyde alone or in combination.

12. The method according to claim 7 or 8 wherein the drug is doxorubicin and the polymer is polyglutaraldehyde.

13. A method for the production of a cytostatic or cytotoxic effect on a target cell, which includes the steps of;
providing a pharmaceutical preparation comprising a drug covalently coupled on the surface of an organic polymer having a diameter in the range of about 100 angstroms to 1.5 microns, which polymer is otherwise biocompatible with the target cell and of a size which prevents transport through the outer membrane of the target cell, said preparation being essentially free of immunoglobulins; and
causing the drug to attach to the outer membrane of the target cell and produce said effect in the essential absence of endocytosis, said drug remaining coupled to the polymer during said effect.

14. The method according to claim 13 wherein the organic polymer is selected from the group consisting of polyglutaraldehyde, polyhydroxyethylmethacrylate, polyacrolein, polymers of a glucuronic acid, polymers of hexose or hexose amines, polyamino acid, or starch or vinyl pyrolidone polymeric beads containing functional groups effecting said covalent coupling.

15. The method according to claim 13 wherein the polymer contains functional group selected from hydroxyl, carboxyl, amine, sulfhydril, azide or aldehyde alone or in combination.

16. The method according to claim 13, 14 or 15 wherein the drug is anti-neoplastic and wherein the target cell has resistance to the drug in an uncoupled form, and said method improves the cytostatic or cytotoxic effect thereof.

17. An analytical method for quantifying the drug sensitivity of a cell, comprising the steps of:
preparing a preparation according to claim 1 wherein said polymer bears a tracer substance;
applying said preparation to a cell; and
measuring, by means for detecting said tracer, the extent to which said reagent is covalently bound to said cell.

18. The method of claim 17 in which said tracer is selected from the group consisting of fluorescent materials, radioactive materials or heavy metals.

* * * * *